(12) United States Patent
Boslough et al.

(10) Patent No.: US 7,938,784 B2
(45) Date of Patent: May 10, 2011

(54) COMPACT DIAGNOSTIC NEUROLOGICAL TOOL

(75) Inventors: James G. Boslough, Billings, MT (US); Erich H. Lubkeman, Billings, MT (US); Benjamin T. Cross, Ritzville, WA (US)

(73) Assignee: J & R Enterprises, Inc., Billings, MT (US)

( * ) Notice: Subject to any disclaimer, the term of this patent is extended or adjusted under 35 U.S.C. 154(b) by 13 days.

(21) Appl. No.: 12/444,395

(22) PCT Filed: Feb. 2, 2007

(86) PCT No.: PCT/US2007/002836
§ 371 (c)(1),
(2), (4) Date: Apr. 5, 2009

(87) PCT Pub. No.: WO2008/048341
PCT Pub. Date: Apr. 24, 2008

(65) Prior Publication Data
US 2010/0106049 A1    Apr. 29, 2010

(51) Int. Cl.
*A61B 19/00* (2006.01)
*A61B 5/00* (2006.01)
*A61B 5/103* (2006.01)
*A61B 5/117* (2006.01)

(52) U.S. Cl. .................. 600/553; 600/552; 600/587

(58) Field of Classification Search .............. 600/300, 600/546, 552–556, 587–595
See application file for complete search history.

(56) References Cited

U.S. PATENT DOCUMENTS

| | | | |
|---|---|---|---|
| 1,269,820 A | 6/1918 | Karatsu | |
| 2,315,160 A | 3/1943 | Newstedt et al. | |
| D136,273 S | 8/1943 | Brandenburg | |
| 2,330,882 A | 10/1943 | Gray | |
| 2,532,093 A | 11/1950 | Golub et al. | |
| 2,908,268 A | 10/1959 | Guest | |
| 3,185,146 A | 5/1965 | Leopoldi | |
| D204,651 S | 5/1966 | Laughlin | |
| 3,344,781 A | 10/1967 | Allen | |
| D209,940 S | 1/1968 | Marsh | |
| 3,515,125 A | 6/1970 | Ruskin | |
| 4,825,874 A * | 5/1989 | Uhlemann | 600/523 |
| 6,406,436 B1 | 6/2002 | Schiffman | |
| 6,510,918 B2 * | 1/2003 | Bates | 181/131 |
| 7,291,116 B2 * | 11/2007 | Kirchner | 600/553 |

* cited by examiner

*Primary Examiner* — Jeffrey G Hoekstra
(74) *Attorney, Agent, or Firm* — Antoinette M. Tease

(57) ABSTRACT

A compact diagnostic neurological tool comprising a two-point discriminator; a brush; and a sharp-dull instrument; wherein the two-point discriminator, the brush, and the sharp-dull instrument are all housed within a case; wherein the two-point discriminator, the brush, and the sharp-dull instrument are all retractable; wherein the two-point discriminator comprises two tines, and wherein the distance between the tines can be increased by extending the two-point discriminator and decreased by retracting the two-point discriminator. The case is preferably rectangular in shape and roughly five inches long, one and one-quarter inches wide, and one-half inch thick.

20 Claims, 14 Drawing Sheets

COMPACT DIAGNOSTIC NEUROLOGICAL TOOL

CROSS-REFERENCE TO RELATED APPLICATION

This application claims priority back to U.S. Patent Application No. 60/851,428 filed on 16 Oct. 2006, the contents of which are incorporated herein by reference.

BACKGROUND OF THE INVENTION

1. Field of the Invention

The present invention relates generally to the field of medical devices, and more specifically, to a compact, hand-held tool that combines various instruments used to diagnose neurological conditions.

2. Description of the Related Art

Neurologists use a number of different instruments to perform various diagnostic functions on their patients, and physicians who are not neurologists (for example, family practitioners or emergency physicians), as well as nurse practitioners and chiropractors, also need to be able to perform neurological tests on occasion. Neurologists may need to perform these tests when they are not in the office and do not have access to their customary supply of instruments. Other health care providers may not have access to all of the neurological diagnostic tools that neurologists have, yet they may be called upon to perform diagnostic neurological tests. In addition, a health care provider may be called upon to perform a diagnostic test rapidly (as, for example, in an emergency room situation), when there is no time to search for the appropriate instrument. For all of these reasons, there is a need for a compact and portable tool that combines various instruments used to perform diagnostic neurological tests. Furthermore, it is preferable to have a tool in which the instruments can be used without being removed from the tool so that they cannot be lost or misplaced. Currently, a physician must carry or have access to a number of different instruments in order to perform these various tests.

The instruments that are used to perform these tests include, but are not limited to, the two-point discriminator, which is used to tell whether a patient can distinguish between two points of contact, the light-touch brush, which is used to determine whether a patient can feel soft touch on the skin, the sharp-dull instrument, which is used to test a patient's ability to distinguish sharp from dull, the Taylor-type and Buck-type hammers, which are used to test a patient's reflexes, and the Wartenberg wheel, which is rolled over a patient's skin on the back, chest or elsewhere to determine the level of a spinal cord lesion. All of these tools exist in prior art, but they have never, to the inventors' knowledge, been combined in a single compact tool as in the present invention.

U.S. Pat. No. 1,269,820 (Karatsu, 1918) deals with one of the first compact neurological diagnostic tools to be patented. This patent describes an esthesiometer, which combines a brush for detecting sensitivity, two blunt-headed surface sensibility detectors, and two needle points slidably mounted inside the detectors.

U.S. Pat. No. 2,315,160 (Newstedt et al., 1943) relates to a compact neurological tool that combines a tuning fork, a percussion head, a brush, and an esthesiometer comprised of two needles pivotally connected to each other. The tuning fork functions as the handle for the percussion head, and the esthesiometer screws onto and is removable from the unit.

U.S. Pat. No. 2,330,882 (Gray, 1943) provides a reflex hammer with a Wartenberg wheel located inside of the hammer head and a handle comprising two pivotable arms that can be used as a two-point discriminator. In contrast to the Marsh design patent discussed below, the handle connects to the hammer head at one end of the hammer head rather than in the center of the hammer head.

U.S. Pat. No. 136,273 (Brandenburg, 1943) provides an ornamental design for a combined neurological hammer, brush and needle. The needle unscrews from the top of the hammer, and the brush unscrews from the hollow handle of the tool.

U.S. Pat. No. 2,532,093 (Golub et al., 1950) covers a neurological hammer With a brush and needles hidden inside of the handle. The brush and needle are both removable from the unit.

U.S. Pat. No. 2,908,268 (Guest, 1959) discloses a neurological diagnostic tool comprising a hammer, scratching element, tuning fork, and measuring tape. The unit optionally comprises extra bores or sockets that may be used for readily insertable and removable accessories, such as a needle or brush.

U.S. Pat. No. 3,185,146 (Leopoldi, 1965) provides a collapsible neurological hammer with a removable brush and pin. The hammer head has a relatively large end and a relatively small end and is pivotable so that the device can be collapsed for storage.

U.S. Pat. No. 3,344,781 (Allen, 1964) describes a multipurposes neurological diagnostic tool comprised of a tuning fork, reflex hammer, Wartenberg wheel, and brush. The tuning fork, hammer, Wartenberg wheel, and brush are all separable from one another.

U.S. Pat. No. D204,651 (Laughlin, 1966) shows a neurological percussion hammer in which a needle and brush are stored within the head of the hammer. The needle and brush are both removable.

U.S. Pat. No. 3,515,125 (Ruskin, 1967) involves a neurological diagnostic tool comprising a disc-shaped hammer head that is moveable to one of two positions relative to the handle. In one position, the hammer head is perpendicular to the handle, and in the other position, it is parallel to the handle. The handle incorporates a Wartenberg wheel and a blunt projection for testing plantar reflexes.

U.S. Pat. No. D209,940 (Marsh, 1968) depicts a neurological diagnostic instrument comprising a hammer head and a handle comprising two pivotable arms that can be used to as a two-point discriminator. A Wartenberg wheel is provided inside one side of the hammer head.

U.S. Pat. No. 6,406,436 (Schiffman, 2002) involves a compact physical examination instrument comprising a battery-operated penlight device, a pin prick mechanism, a reflex hammer and/or measuring device, and a vibratory mechanism. The pin prick mechanism includes a rotatable and completely removable pin dispenser carousel. The reflex hammer head is preferably rotatable and circular so that it can also be used to measure distance.

BRIEF SUMMARY OF THE INVENTION

The present invention is a compact diagnostic neurological tool comprising a two-point discriminator; a brush; and a sharp-dull instrument; wherein the two-point discriminator, the brush, and the sharp-dull instrument are all housed within a case; wherein the two-point discriminator, the brush, and the sharp-dull instrument are all retractable; wherein the two-point discriminator comprises two tines, and wherein the distance between the tines can be increased by extending the two-point discriminator and decreased by retracting the two-point discriminator. The case is preferably rectangular in shape and roughly five inches long, one and one-quarter inches wide, and one-half inch thick.

The present invention further comprises thumb grips that enable the two-point discriminator, the brush, and the sharp-dull instrument to be extended outside of the case or retracted into the case. In a preferred embodiment, the present invention further comprises a hinge, wherein the hinge is located on the top end of the tool, wherein the brush and the sharp-dull instrument are adjacent one another, wherein the two-point discriminator is located adjacent to a swing arm when the swing arm is in a closed position, wherein the swing arm can be pivoted upward on the hinge until the swing arm is parallel to and directly above the two-point discriminator, and wherein the swing arm comprises a Wartenberg wheel. The swing arm optionally comprises a weight.

In a preferred embodiment, the present invention further comprises a Buck-type hammer, wherein the swing arm comprises a top end, and wherein the Buck-type hammer is located on the outside of the case on the top end of the swing arm when the swing arm is in a closed position. In yet another preferred embodiment, the present invention further comprises a Taylor-type hammer, wherein the Taylor-type hammer is located on the outside of the case directly adjacent to the two-point discriminator. Preferably, the case functions as the handle of the hammer.

The brush and sharp-dull instrument preferably exit from the bottom end of the tool when in an extended position, and the two-point discriminator preferably exits from the top end of the tool when in an extended position. Preferably, neither the two-point discriminator, the brush, nor the sharp-dull instrument is removable.

In a preferred embodiment, the present invention further comprises a pocket clip located on the back side of the tool. In yet another preferred embodiment, the present invention further comprises a pocket clip, wherein the top end of the pocket clip is attached to the top end of the tool, and wherein the hinge and the top end of the pocket clip form a blunt end that can be used to test plantar stimulation when the swing arm is closed.

In a preferred embodiment, the swing arm further comprises a light, a light switch, a battery cover, and a battery, and wherein the battery cover is removable. Preferably, the Wartenberg wheel can be removed and replaced when the battery cover is removed.

In a preferred embodiment, the present invention further comprises a scale that can be used for general measurement purposes and that extends along one side of the case. In yet another preferred embodiment, the present invention further comprises a scale that can be used for general measurement purposes, wherein the scale extends along one side of the case from the Buck-type hammer to the bottom end of the tool when the swing arm is in a closed position. The present invention optionally comprises a pupil dilation chart located on the back side of the tool.

In a preferred embodiment, the thumb grips are located on the front side of the case, and the case is slightly concave in shape such that the front side of the case is curved inward to facilitate use of the thumb grips.

REFERENCE NUMBERS

Figure 1:
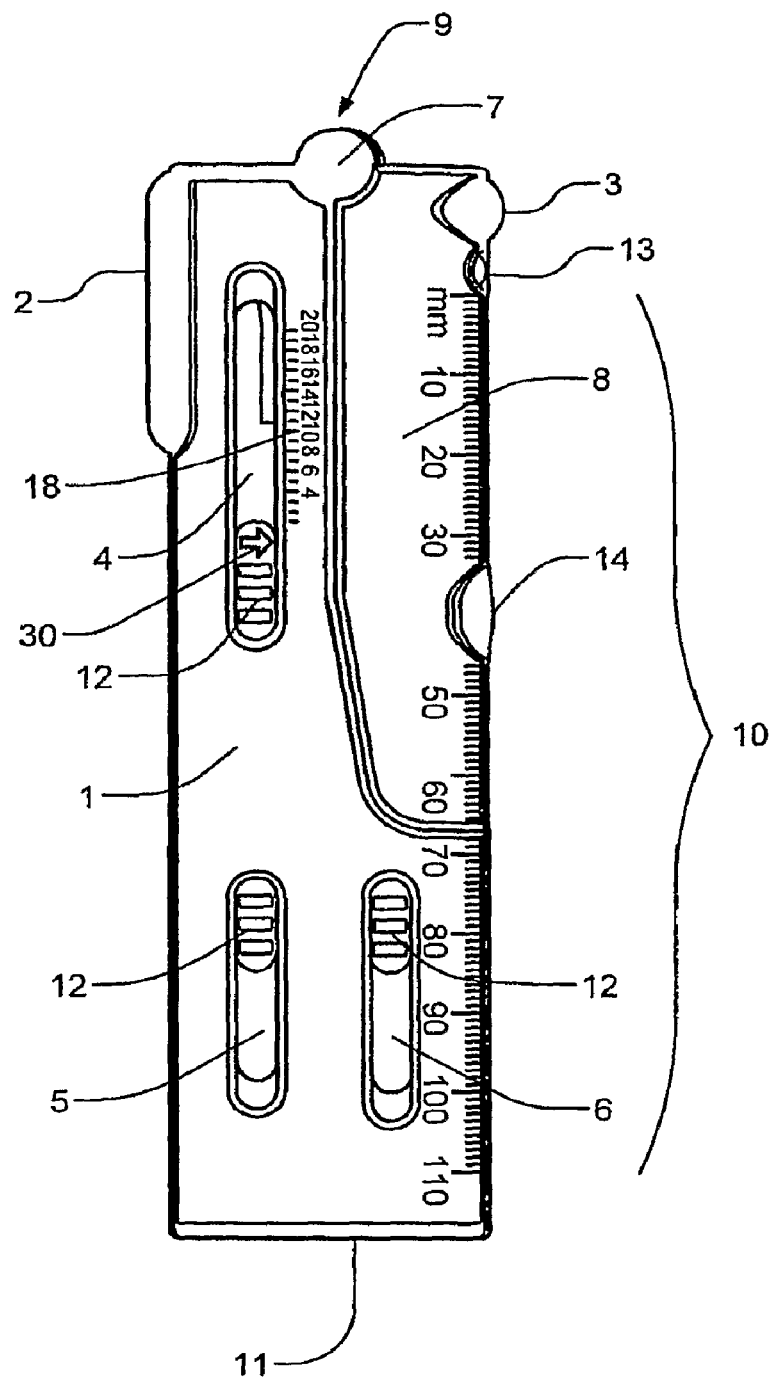
FIG. 1 is a front view of the present invention.

1 Case
2 Taylor-type hammer
3 Buck-type hammer
4 Variable two-point discriminator
5 Light-touch brush
6 Sharp-dull instrument
7 Hinge (of swing arm)
8 Swing arm
9 Blunt end (for plantar stimulation)
10 Scale (for general measurement purposes)
11 Bottom end (of tool)
12 Thumb grip
13 Light
14 Light switch
15 Pocket clip
16 Pupil dilation chart
17 Tines (of two-point discriminator)
18 Scale (of two-point discriminator)
19 Tine with sharp end (of sharp-dull instrument)
20 Tine with dull end (of sharp-dull instrument)
21 Wartenberg wheel
22 Recess (for receiving Wartenberg wheel)
23 Protrusion
24 Dimple
25 Battery cover
26 Battery
27 Receptacle
28 Axle (of Wartenberg wheel)
29 Top end (of tool)
30 Arrow (on thumb grip)
31 Finger grip (on battery cover)
32 Cutout
33 Slide
34 Rail
35 First ball spring
36 Second ball spring
37 Indentation (in hinge)

DETAILED DESCRIPTION OF INVENTION

FIG. 1 is a front view of the compact diagnostic neurological tool of the present invention. As shown in this figure, the invention comprises a rectangular case 1 that houses the various instruments that comprise the present invention. Those instruments include a Taylor-type hammer 2, a Buck-type hammer 3, a variable two-point discriminator 4, a light-touch brush 5, and a sharp-dull instrument 6. The variable two-point discriminator 4, light-touch brush 5, and sharp-dull instrument 6 are all retractable, and in this figure, they are shown in a retracted position. None of these instruments is removable, and all of the instruments can be used without being removed from the tool itself. As shown better in FIG. 11, the top of the pocket clip 15 (see FIG. 2) and the hinge 7 of the swing arm 8 form a blunt end 9 that can be used for plantar stimulation and testing the Babinski reflex. In addition, the tool preferably comprises a scale 10 that is provided on the right-hand side of the tool between the Buck-type hammer 3 and the bottom end 11 of the tool.

In a preferred embodiment, the tool is approximately five inches long, approximately one and one-quarter inches wide, and approximately one-half inch thick. The Taylor-type 2 and Buck-type 3 hammers are used to test a patient's reflexes, and the case 1 serves as the handle of the hammer. Each hammer is comprised of a membrane that is made of rubber or another suitable material. The membrane is permanently attached to the outside of the case 1. The variable two-point discriminator 4 is used to test a patient's ability to distinguish between two points of contact. The light-touch brush 5 is used to determine whether a patient can feel soft touch on the skin, and the sharp-dull instrument 6 is used to test a patient's ability to distinguish sharp from dull. The scale 10 can be used for measurement purposes and is preferably in millimeters (mm). A tool that is roughly five inches long will accommodate a 110-mm scale. Thumb grips 12 are provided for operation of the variable two-point discriminator 4, light-touch brush 5, and sharp-dull instrument 6. The thumb grips 12 allow these three instruments to be retracted or extended, as shown in FIGS. 3-6.

Figure 8:
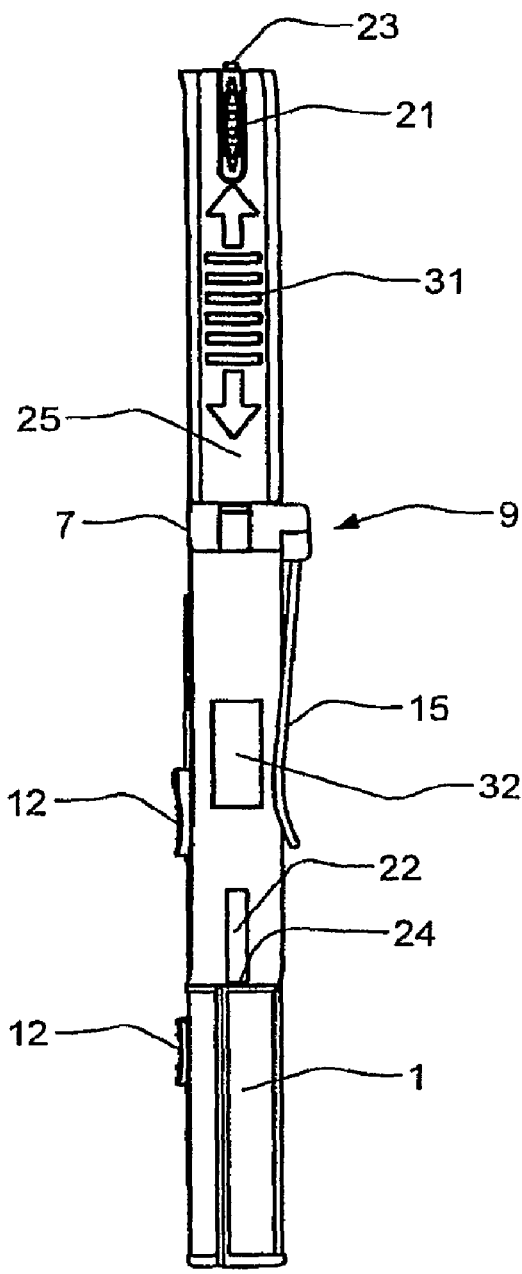
FIG. 8 is a side view of the present invention with the swing arm fully extended.
Figure 8A:
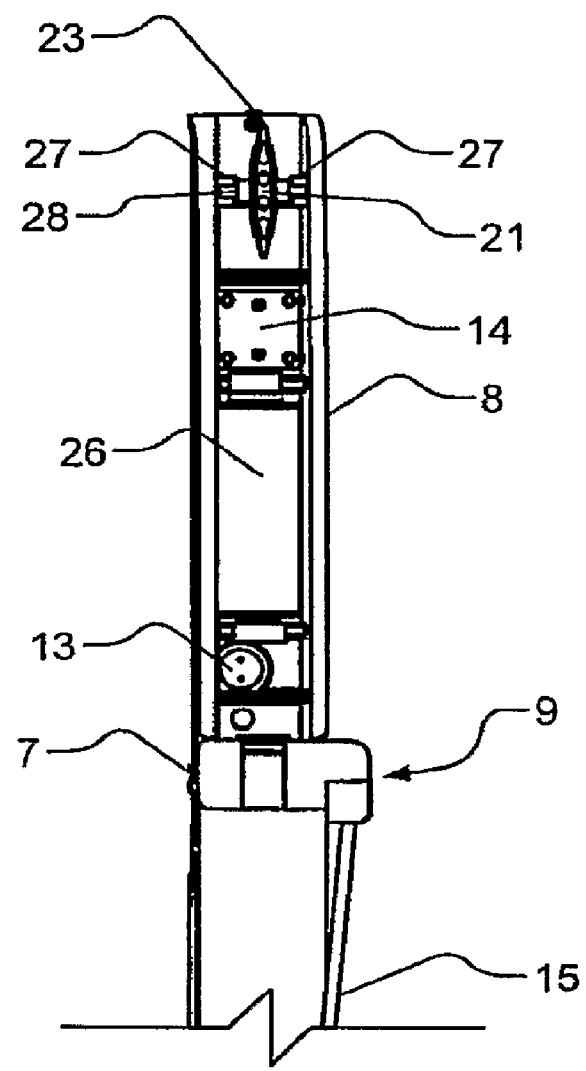
FIG. 8A is a partial side view of the present invention with the swing arm fully extended but without the battery cover.

The tool preferably comprises a light 13, which is situated directly underneath the Buck-type hammer 3. As shown in FIG. 8A, the light 13 is battery-operated, and the battery is housed inside of the swing arm 8. The light switch 14 is also located on the swing arm 8. The switch is preferably one that activates the light only as long as pressure is applied to the switch; when the pressure is relieved, the light will turn off.

Figure 2:
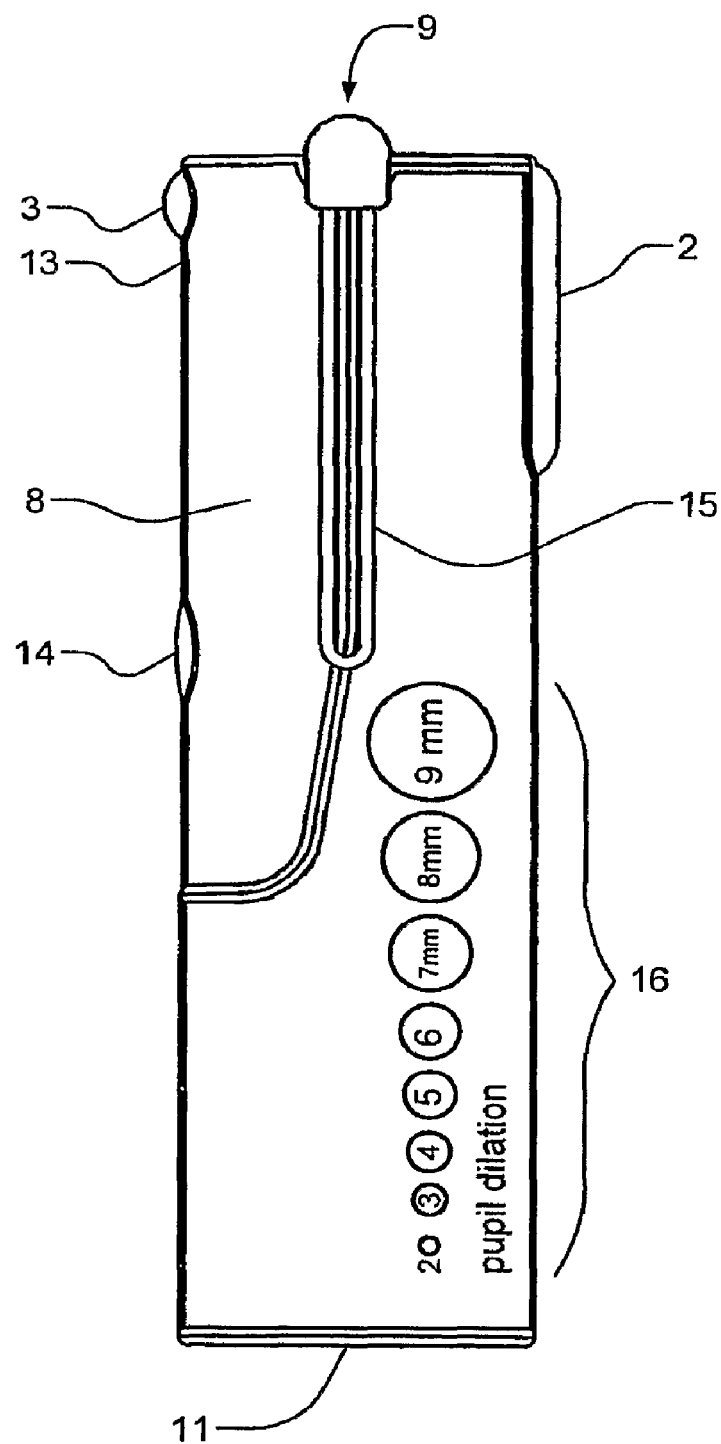
FIG. 2 is a back view of the present invention.

FIG. 2 is a back view of the present invention. As shown in this figure, the invention comprises a pocket clip 15 that can be used to clip the tool onto a pocket. Provided on the back of the tool is an optional pupil dilation chart 16 that allows a physician to measure pupil dilation from two to nine mm.

Figure 3:
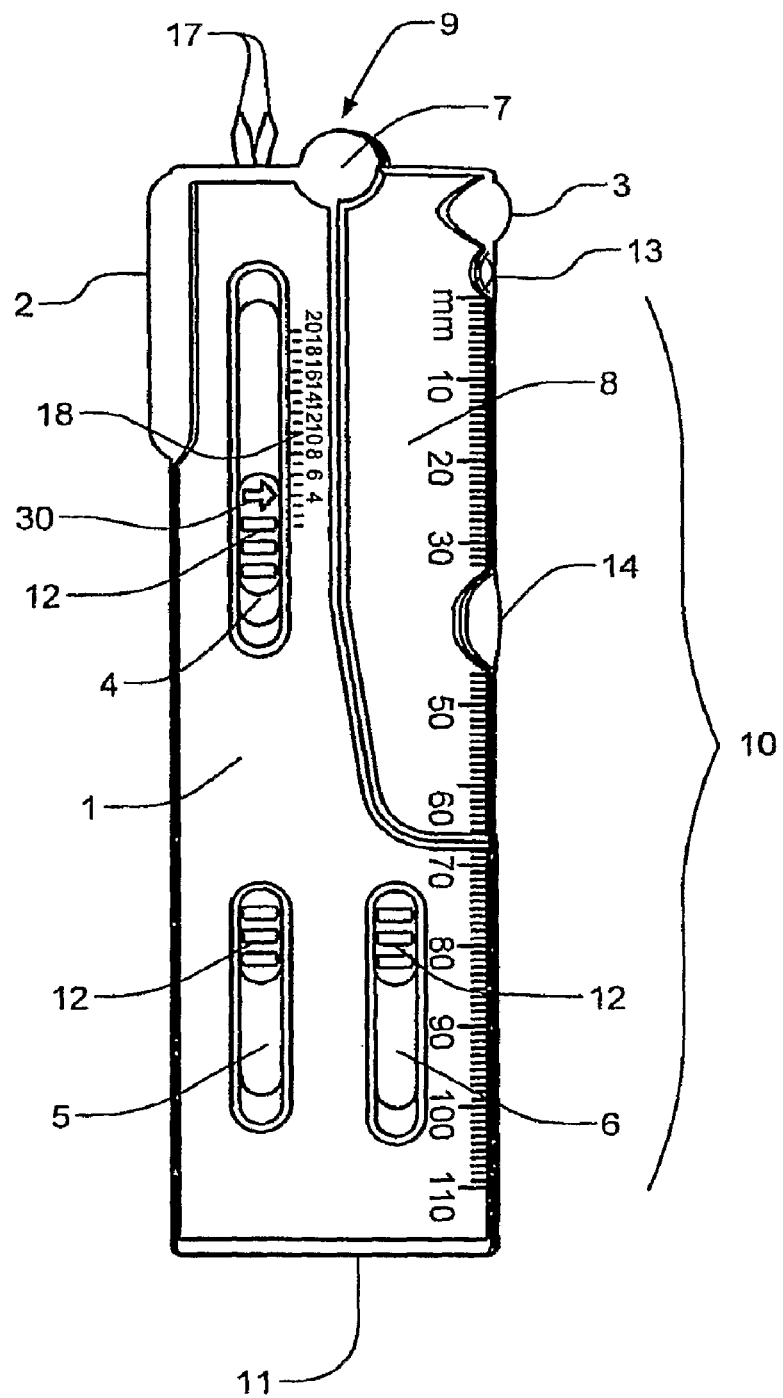
FIG. 3 is a front view of the present invention with the two-point discriminator partially extended.
Figure 4:
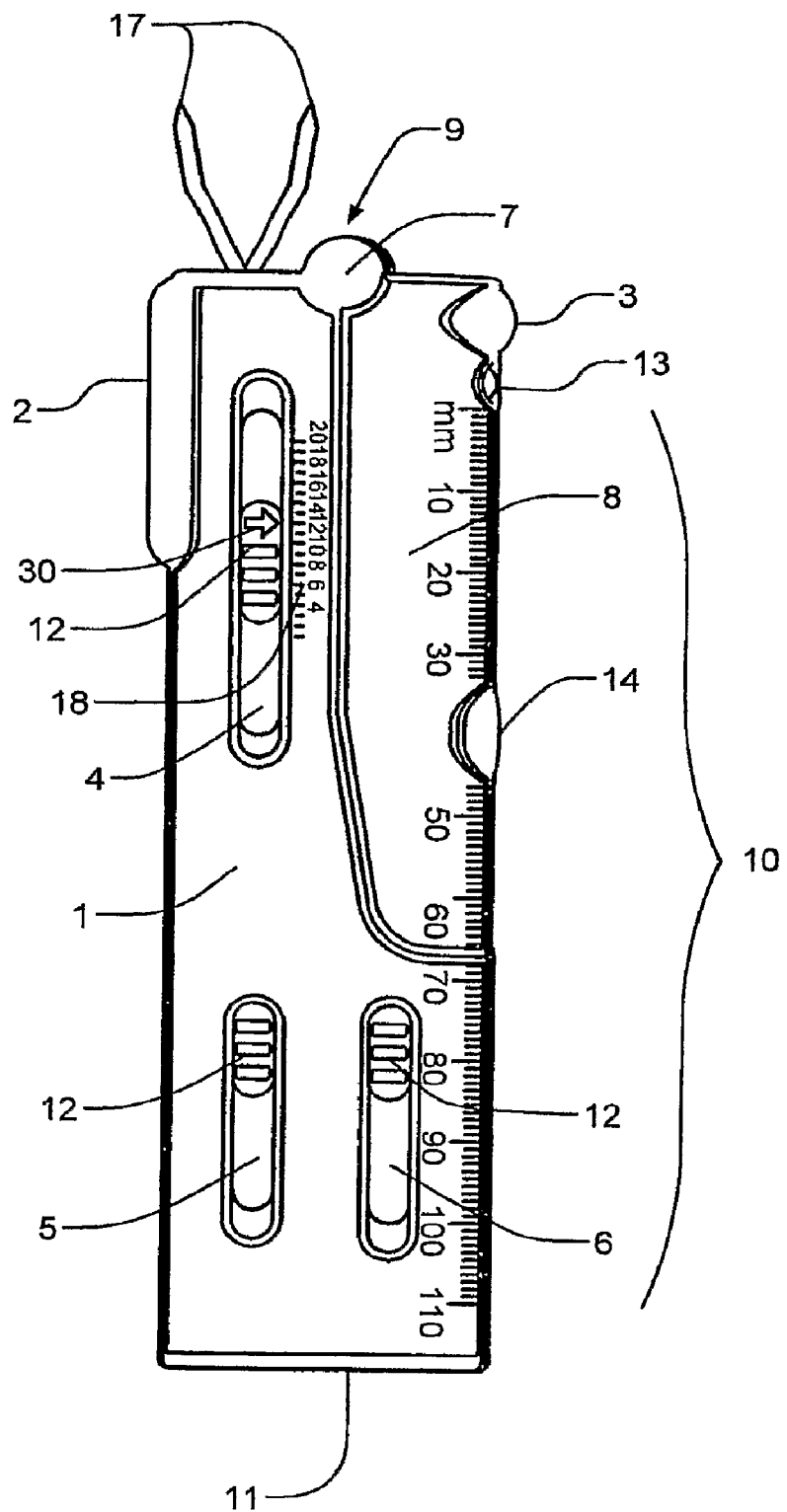
FIG. 4 is a front view of the present invention with the two-point discriminator further extended than in FIG. 3.
Figure 5:
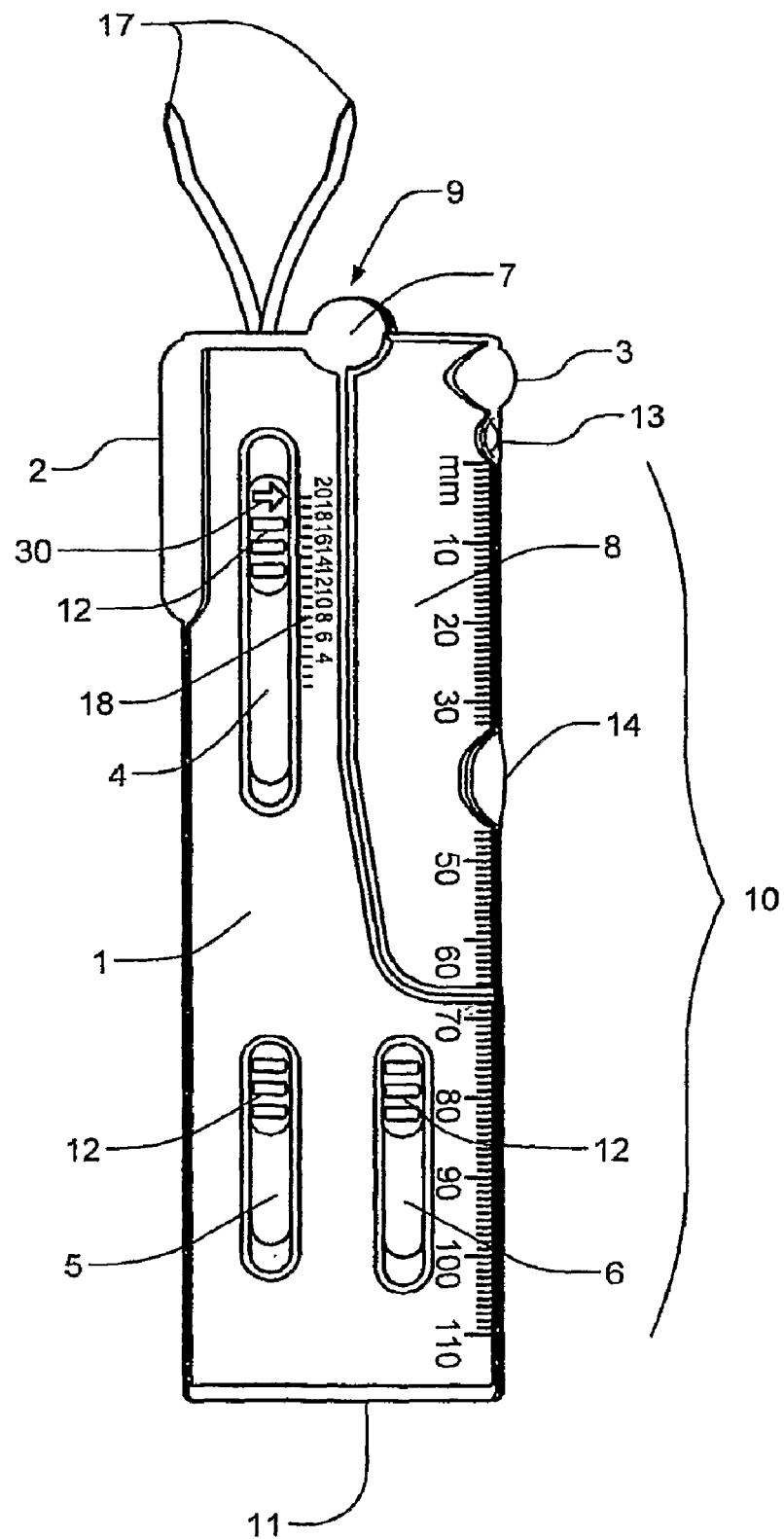
FIG. 5 is a front view of the present invention with the two-point discriminator fully extended.

FIG. 3 is a front view of the present invention with the variable two-point discriminator 4 partially extended. As shown in this figure, the two-point discriminator 4 comprises two tines 17. The two-point discriminator is called a "variable" two-point discriminator because the distance between the two tines is determined by the user. As the thumb grip 12 is pushed upward, the two tines 17 move increasingly apart from one another, as shown in FIGS. 4 (two-point discriminator further extended than in FIG. 3) and 5 (two-point discriminator fully extended). When the two-point discriminator 4 is fully extended, the tines are preferably 20 mm apart. As the thumb grip 12 is moved downward, the tines 17 move more closely together. The two-point discriminator 4 preferably includes a scale 18 situated adjacent to the thumb grip 12 that corresponds to the distance between tines 17. The thumb grip 12 preferably comprises an arrow 30 that is slightly raised and that points to the scale 18 to indicate the distance between the tines 17 on the two-point discriminator 4.

Figure 6:
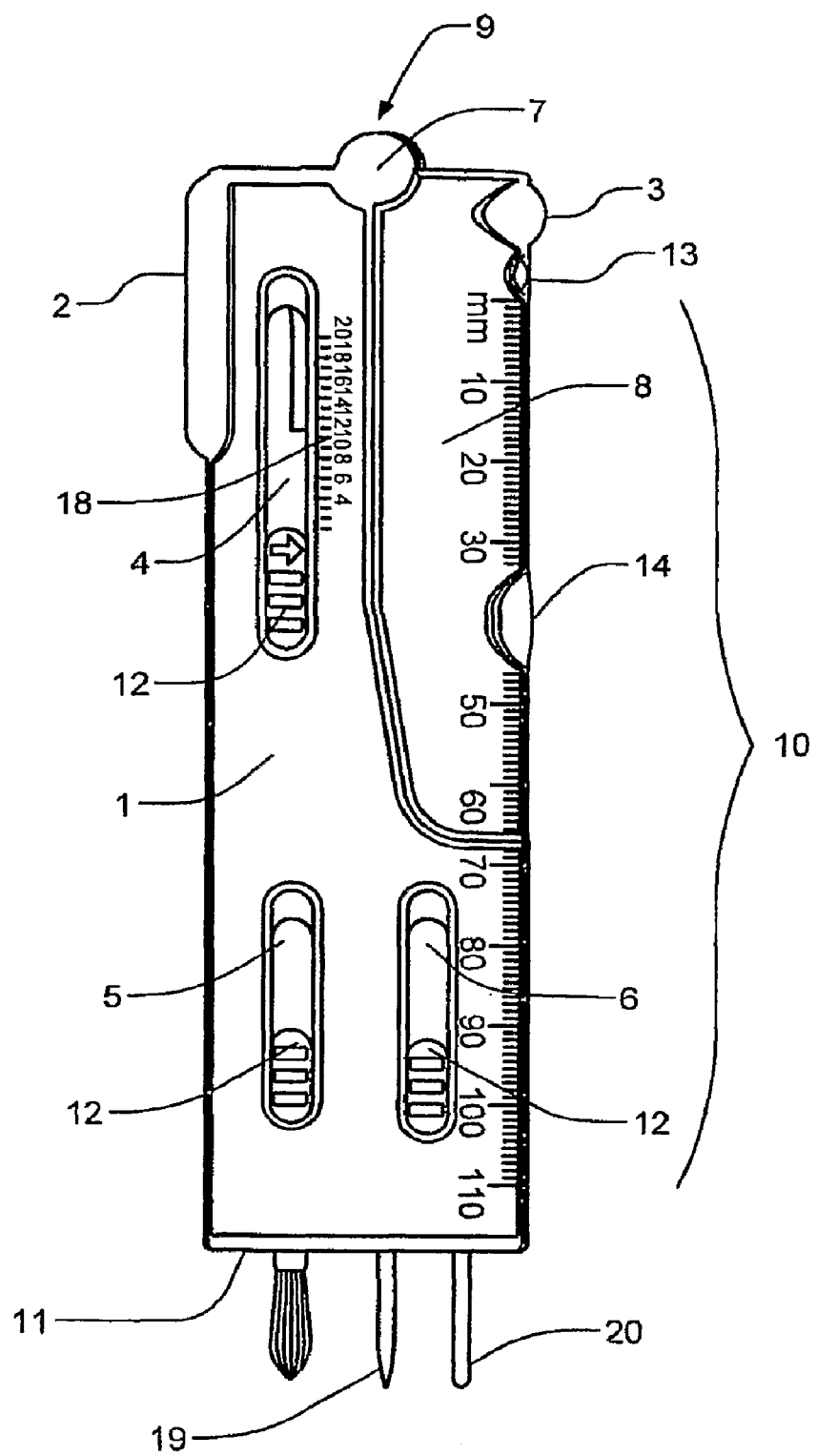
FIG. 6 is a front view of the present invention with the light-touch brush and sharp-dull instrument extended.

FIG. 6 is a front view of the present invention with the light-touch brush 5 and sharp-dull instrument 6 extended. Both the brush 5 and the sharp-dull instrument 6 are extended by moving the thumb grips 12 toward the bottom end 11 of the case 1. The brush 5 and sharp-dull instrument 6 are retracted by moving the thumb grips 12 in the opposite direction (back to the position shown in FIG. 1). As shown in this figure, the sharp-dull instrument 6 comprises a tine with a sharp end 19 and a tine with a dull end 20. These two tines are preferably at a constant distance from one another and not a variable distance, as with the two-point discriminator.

Figure 7:
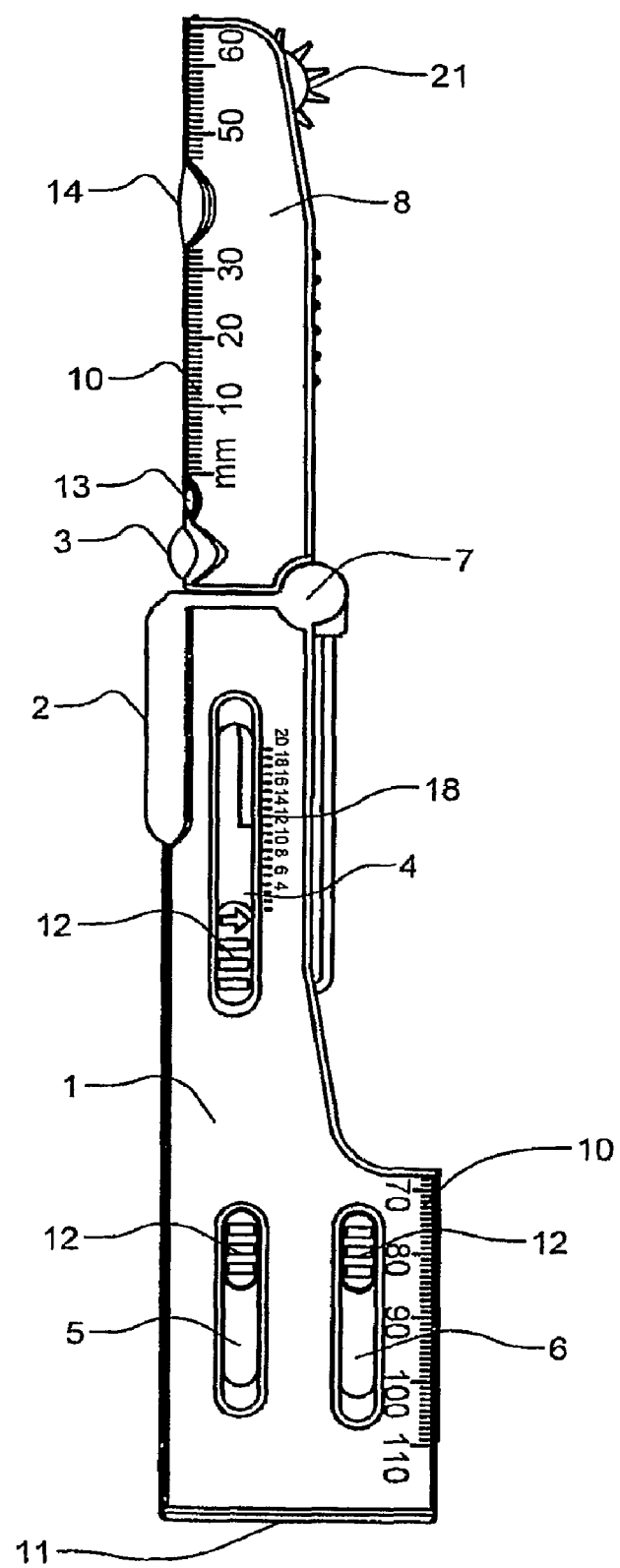
FIG. 7 is a front view of the present invention with the swing arm fully extended.

FIG. 7 is a front view of the present invention with the swing arm 8 fully extended. The swing arm 8 pivots on the hinge 7 until the Buck-type hammer 3 is adjacent to the Taylor-type hammer 2. At that point, the swing arm 8 is parallel with the left-hand side of the case 1. As shown in this figure, inside the swing arm 8 is a Wartenberg wheel 21. FIG. 8 is a side view of the present invention with the swing arm 8 fully extended. When the swing arm 8 is closed (as shown in FIGS. 1-6), the Wartenberg wheel 21 fits into a recess 22 in the case 1, and a protrusion 23 on the tip of the swing arm 8 fits into a dimple 24 in the case 1, thereby locking the swing arm 8 in a closed position.

FIG. 8 also shows the battery cover 25 that extends across the inner surface of the swing arm 8. The battery cover 25 can be removed by sliding the cover upward toward the wheel and lifting it out. An optional raised finger grip 31 makes it easier for the user to slide the battery cover 25 off. An optional cutout 32 in the inside of the case 1 accommodates the raised finger grip 31 and prevents the swing arm 8 from sliding side to side when it is closed.

FIG. 8A shows what lies beneath the battery cover 25. As shown in this figure, the swing arm 8 houses the light 13, a battery 26, and the light switch 14. Preferably, two receptacles 27 extend inwardly from the inside of the swing arm 8, and each end of the axle 28 of the Wartenberg wheel 21 lies in one of the receptacles 27. In this manner, the Wartenberg wheel 21 can be easily removed, for example, to allow for disposable wheels to be used, to switch from a plastic wheel to a stainless steel wheel or vice versa, or to substitute different sized wheels (though the wheel must fit within the recess 22 in the case 1). When the battery cover 25 is reinstalled, the receptacles 27 are covered (see FIG. 8), and the wheel cannot be removed. A weight (not shown) may be added to the swing arm if additional weight is desired to provide the hammers with optimal performance.

Figure 9:
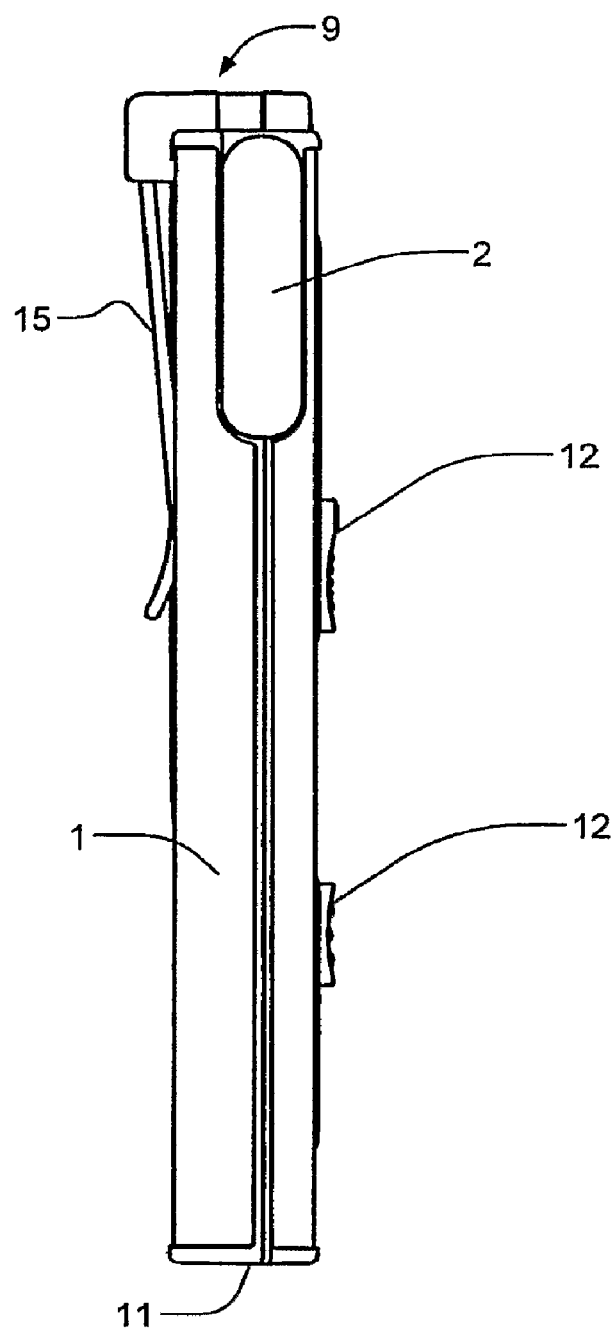
FIG. 9 is a first side view of the present invention with the swing arm closed.
Figure 10:
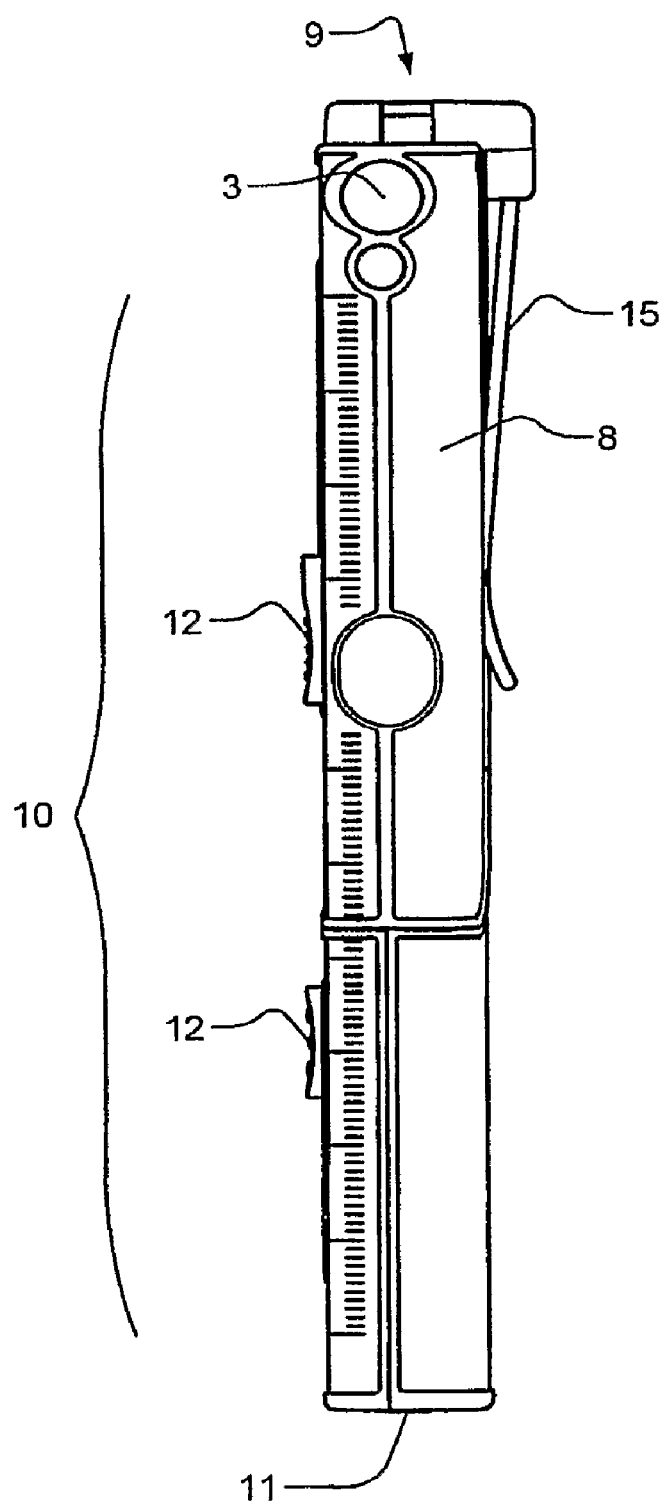
FIG. 10 is a second side view of the present invention with the swing arm closed.

FIG. 9 is a first side view of the present invention with the swing arm closed, and FIG. 10 is a second side view of the present invention with the swing arm closed. The features shown in both of these figures have been discussed above.

Figure 11:
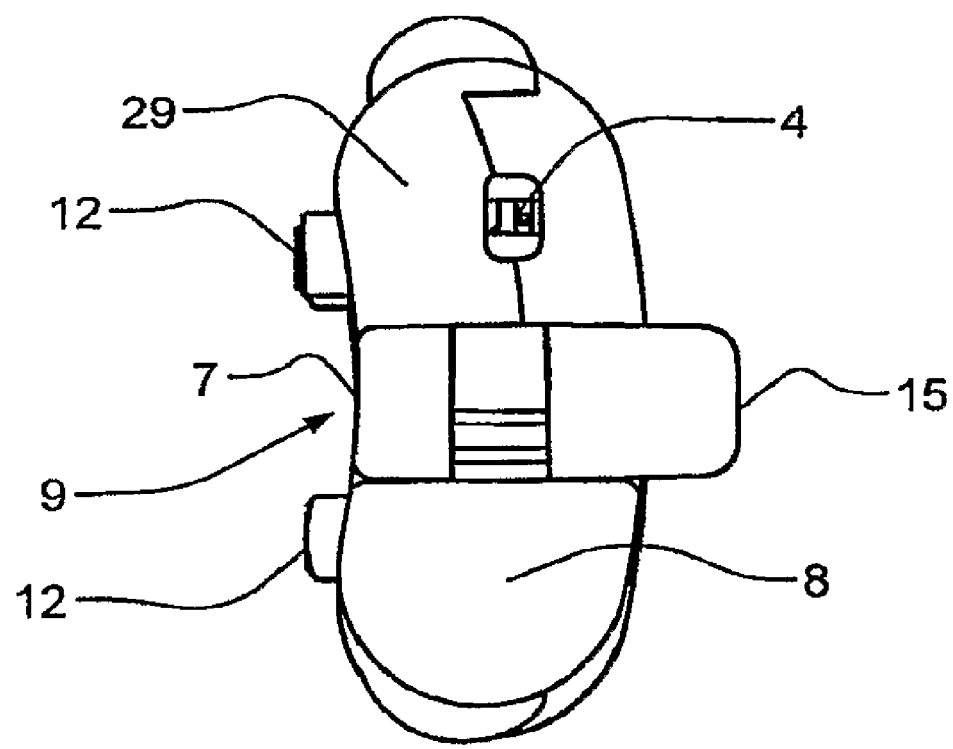
FIG. 11 is a top view of the present invention with the swing arm closed.

FIG. 11 is a top view of the present invention with the swing arm 8 closed. This figure shows the blunt end 9 of the tool, which is used for plantar stimulation. The blunt end 9 is preferably comprised of the swing arm hinge 7 and the top of the pocket clip 15. This figure also shows the exit point for the variable two-point discriminator 4.

Figure 12:
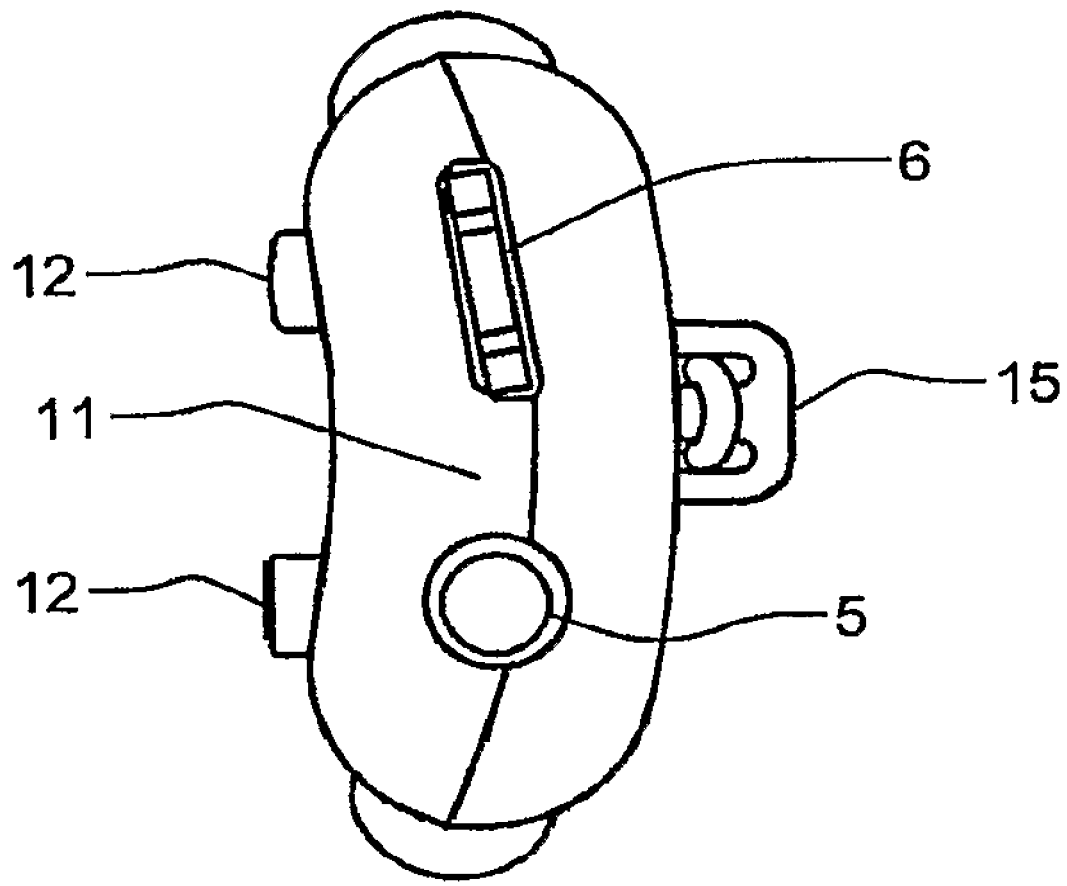
FIG. 12 is a bottom view of the present invention.

FIG. 12 is a bottom view of the present invention. This figure shows the exit points for the light-touch brush 5 and the sharp-dull instrument 6. As shown in FIGS. 11 and 12, the tool is preferably slightly concave in shape (i.e., curving inward toward the thumb grips) to provide for a more comfortable hold when using the thumb grips 12.

Figure 13:
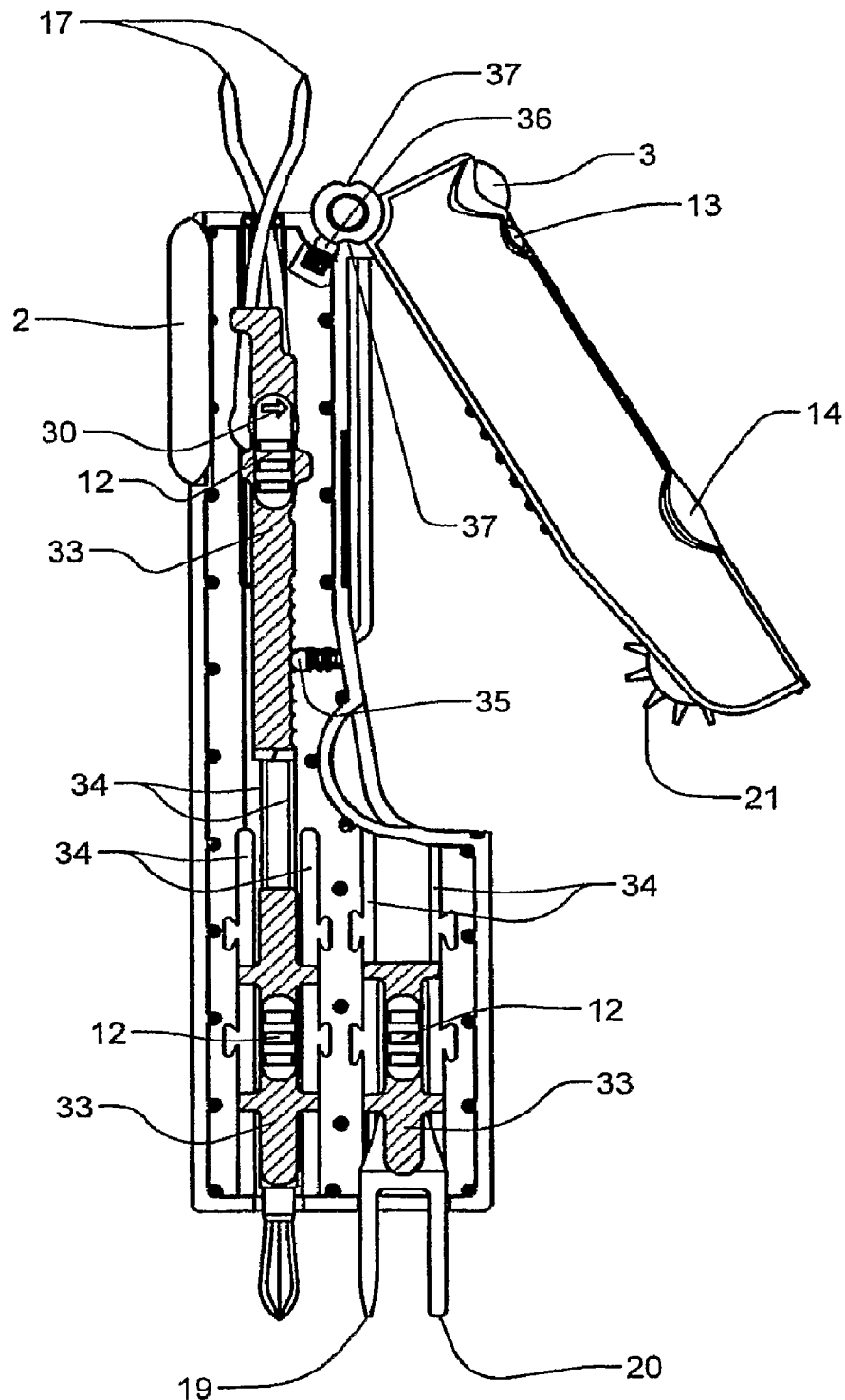
FIG. 13 is a front view of the present invention with the case removed for illustration purposes and the swing arm partially open.

FIG. 13 is a front view of the present invention with the case 1 removed for illustration purposes and the swing arm 8 partially open. As shown in this figure, the variable two-point discriminator 4, brush 5 and sharp-dull instrument 6 each comprises a slide 33 that allows the two-point discriminator 4, brush 5 and sharp-dull instrument 6 to be retracted or extended. The thumb grips 12 are attached to the slides 33, and the slides 33 in turn are slidably attached to rails 34 on the inside of the case 1. A first ball spring 35 controls the sliding movement of the two-point discriminator 4 and ensures that its position corresponds to the measurements indicated on the scale 18 (not shown) on the outside of the case 1. A second ball spring 36 kicks the swing arm into place when it is either fully extended (as shown in FIG. 7) or fully closed (as shown in FIG. 1) by engaging indentations 37 in the hinge 7.

Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A compact diagnostic neurological tool comprising:
    (a) a variable two-point discriminator;
    (b) a brush; and
    (c) a sharp-dull instrument having a fine with a pointed end and a fine with a blunt end, wherein the tines are at a constant distance from one another;
    wherein the variable two-point discriminator, the brush, and the sharp-dull instrument are all housed within a single case;
    wherein the variable two-point discriminator, the brush, and the sharp-dull instrument may be retracted so that they are fully enclosed by the case or extended so that they extend outside of the case;
    wherein the variable two-point discriminator comprises two tines with distal ends, and wherein the distance between the distal ends of the fines can be increased by the user by pushing a thumb grip upward to extend the two-point discriminator outward from the case and decreased by the user by moving the thumb grip downward to retract the two-point discriminator into the case, and wherein a scale situated adjacent to the thumb grip corresponds to the distance between the distal ends of the tines; and
    wherein neither the variable two-point discriminator, the brush, nor the sharp-dull instrument is removable from the case, the two-point discriminator, the brush, the sharp-dull instrument, and a Whartenberg wheel are all fully enclosed within the case when not in use, and the variable two-point discriminator, the brush, and the sharp-dull instrument are used without being removed from the case.

2. The compact diagnostic neurological tool of claim 1, wherein the case is rectangular in shape.

3. The compact diagnostic neurological tool of claim 1, further comprising thumb grips that enable the brush and the sharp-dull instrument to be extended outside of the case or retracted into the case.

4. The compact diagnostic tool of claim 3, wherein the tool comprises a front side, wherein the thumb grips are located on the front side of the case, and wherein the case is concave in shape such that the front side of the case is curved inward to facilitate use of the thumb grips.

5. The compact diagnostic neurological tool of claim 1, further comprising a hinge, wherein the tool comprises a top end, wherein the hinge is located on the top end of the tool, wherein the brush and the sharp-dull instrument are adjacent one another, wherein the two-point discriminator is located adjacent to a swing arm when the swing arm is in a closed position, wherein the swing arm can be pivoted upward on the hinge until the swing arm is parallel to and directly above the two-point discriminator, and wherein the swing arm comprises the Wartenberg wheel.

6. The compact diagnostic tool of claim 5, further comprising a Buck-type hammer, wherein the swing arm comprises a top end, and wherein the Buck-type hammer is located on the outside of the case on the top end of the swing arm when the swing arm is in a closed position.

7. The compact diagnostic neurological tool of claim 6, further comprising a Taylor-type hammer, wherein the Taylor-type hammer is located on the outside of the case directly adjacent to the two-point discriminator.

8. The compact diagnostic tool of claim 6 or 7, wherein the case functions as the handle of the hammer.

9. The compact diagnostic tool of claim 6, further comprising a scale, wherein the tool comprises a bottom end, and wherein the scale extends along one side of the case from the Buck-type hammer to the bottom end of the tool when the swing arm is in a closed position.

10. The compact diagnostic tool of claim 5, further comprising a pocket clip, wherein the tool comprises a top end, wherein the pocket clip comprises a top end, wherein the top end of the pocket clip is attached to the top end of the tool, and wherein the hinge and the top end of the pocket clip form a blunt end that can be used to test plantar stimulation when the swing arm is closed.

11. The compact diagnostic tool of claim 5, wherein the swing arm further comprises a light, a light switch, a battery cover, and a battery, and wherein the battery cover is removable.

12. The compact diagnostic tool of claim 11, wherein the Wartenberg wheel can be removed and replaced when the battery cover is removed.

13. The compact diagnostic tool of claim 5, wherein the swing arm further comprises a weight.

14. The compact diagnostic neurological tool of claim 1, wherein the tool comprises a bottom end, and wherein the brush and sharp-dull instrument exit from the bottom end of the tool when in an extended position.

15. The compact diagnostic neurological tool of claim 1, wherein the tool comprises a top end, and wherein the two-point discriminator exits from the top end of the tool when in an extended position.

16. The compact diagnostic tool of claim 1, wherein neither the two-point discriminator, the brush, nor the sharp-dull instrument is removable.

17. The compact diagnostic tool of claim 1, further comprising a pocket clip, wherein the tool comprises a back side, and wherein the pocket clip is located on the back side of the tool.

18. The compact diagnostic tool of claim 1, further comprising a scale that extends along one side of the case.

19. The compact diagnostic tool of claim 1, wherein the tool comprises a back side, further comprising a pupil dilation chart located on the back side of the tool.

20. The compact diagnostic tool of claim 1, wherein the case is approximately five inches long, one and one-quarter inches wide, and one-half inch thick.

* * * * *